United States Patent
Kodakari et al.

(10) Patent No.: US 10,494,317 B2
(45) Date of Patent: Dec. 3, 2019

(54) DEHYDROGENATION CATALYST FOR ALKYLAROMATIC COMPOUND, PROCESS FOR PRODUCING SAME, AND DEHYDROGENATION METHOD USING SAME

(71) Applicant: Clariant Catalysts (Japan) K.K., Tokyo (JP)

(72) Inventors: Nobuaki Kodakari, Toyama (JP); Shinya Hirahara, Toyama (JP); Yuma Kuraguchi, Toyama (JP); Takashi Kusaba, Toyama (JP)

(73) Assignee: CLARIANT CATALYSTS (JAPAN) K.K., Tokyo (JP)

( * ) Notice: Subject to any disclaimer, the term of this patent is extended or adjusted under 35 U.S.C. 154(b) by 0 days.

(21) Appl. No.: 15/780,681

(22) PCT Filed: Dec. 8, 2016

(86) PCT No.: PCT/JP2016/086489
§ 371 (c)(1),
(2) Date: Jun. 1, 2018

(87) PCT Pub. No.: WO2017/099161
PCT Pub. Date: Jun. 15, 2017

(65) Prior Publication Data
US 2018/0370872 A1    Dec. 27, 2018

(30) Foreign Application Priority Data
Dec. 11, 2015   (JP) ................................. 2015-242207

(51) Int. Cl.
*B01J 23/89*   (2006.01)
*C07C 5/333*   (2006.01)
(Continued)

(52) U.S. Cl.
CPC ............. *C07C 5/3332* (2013.01); *B01J 23/83* (2013.01); *B01J 23/8993* (2013.01);
(Continued)

(58) Field of Classification Search
CPC ........ B01J 23/83; B01J 23/89; B01J 23/8993; C07C 5/3332; C07C 2523/83; C07C 2523/89
(Continued)

(56) References Cited

U.S. PATENT DOCUMENTS

| 4,460,706 A | 7/1984 | Imanari et al. |
| 5,023,225 A | 6/1991 | Williams et al. |

(Continued)

FOREIGN PATENT DOCUMENTS

| CN | 10-2040463 | * | 5/2011 | ............ B01J 23/888 |
| CN | 102040463 A |  | 5/2011 |  |

(Continued)

OTHER PUBLICATIONS

International Search Report with Written Opinion of the International Searching Authority completed Jan. 24, 2017 with respect to International Application No. PCT/JP2016/086489.

(Continued)

*Primary Examiner* — Patricia L. Hailey
(74) *Attorney, Agent, or Firm* — Scott R. Cox (57) ABSTRACT

A catalyst which is highly active in dehydrogenation reaction of an alkylaromatic hydrocarbon not only in high-temperature regions (e.g. 600 to 650° C.) as found in the inlet of a catalyst bed in an apparatus for the production of SM but also in low-temperature regions (e.g. under 600° C.) as found in the outlet of a catalyst bed in an apparatus for the production of SM, where the temperature decreases as a result of endothermic reaction; and a process for producing the catalyst; and a dehydrogenation process using the catalyst.

(Continued)

The catalyst contains iron (Fe), potassium (K), and cerium (Ce), and at least one rare earth element other than cerium.

23 Claims, 1 Drawing Sheet

(51) Int. Cl.
    *B01J 23/83*     (2006.01)
    *B01J 37/00*     (2006.01)
    *B01J 37/04*     (2006.01)
    *B01J 37/08*     (2006.01)

(52) U.S. Cl.
    CPC ........... *B01J 37/0009* (2013.01); *B01J 37/04* (2013.01); *B01J 37/08* (2013.01); *C07C 2523/83* (2013.01); *C07C 2523/89* (2013.01)

(58) Field of Classification Search
    USPC .......................... 502/302, 304, 316, 317, 338
    See application file for complete search history.

(56) References Cited

U.S. PATENT DOCUMENTS

| | | |
|---|---|---|
| 5,668,075 A | 9/1997 | Milam et al. |
| 5,962,757 A | 10/1999 | Milam et al. |
| 8,809,609 B2 | 8/2014 | Mishima et al. |
| 2006/0106268 A1 | 5/2006 | Kowaleski |
| 2009/0062588 A1* | 3/2009 | Kowaleski ............ B01J 23/002 585/663 |
| 2010/0087694 A1 | 4/2010 | Mishima |
| 2011/0213189 A1* | 9/2011 | Mishima ............... C07C 5/3332 585/443 |
| 2013/0053608 A1 | 2/2013 | Mishima |
| 2013/0165723 A1* | 6/2013 | Patcas ................. B01J 23/8892 585/444 |

FOREIGN PATENT DOCUMENTS

| | | |
|---|---|---|
| CN | 102371161 A | 3/2012 |
| RU | 2187364 C2 | 8/2002 |

OTHER PUBLICATIONS

Official Report of EAPO dated Jan. 23, 2019 corresponding to Eurasian Patent Application No. 2018 91389 with respect to International Application No. PCT/JP2016/086489.

Supplementary European Search Report completed Jul. 2, 2019 with respect to corresponding EP Application No. 16873054.7 (International Application No. PCT/JP2016/086489).

English translation of Official Report of EAPO dated Aug. 23, 2019 corresponding to Eurasian Patent Application No. 2018 91389 with respect to International Application No. PCT/JP2016/086489. References cited therein have already been disclosed.

English translation of GCC Examination Report dated Jul. 4, 2019 with respect to GCC 2017-33510, potentially related application. References cited therein have already been disclosed.

* cited by examiner

DEHYDROGENATION CATALYST FOR ALKYLAROMATIC COMPOUND, PROCESS FOR PRODUCING SAME, AND DEHYDROGENATION METHOD USING SAME

TECHNICAL FIELD

The present invention relates to a catalyst to be used in a process for producing an alkenylaromatic compound through dehydrogenation reaction by contacting an alkylaromatic compound diluted with water vapor with the catalyst, and a process for producing the same, and a dehydrogenation process using the same.

BACKGROUND OF INVENTION

Styrene monomer (SM) as an alkenylaromatic compound is typically produced through dehydrogenation of ethylbenzene, this production increasing year after year for using said SM as a raw material monomer for synthetic rubbers, ABS resins, polystyrene, etc. The dehydrogenation reaction of ethylbenzene is an endothermic reaction accompanied by volume expansion as represented by reaction formula (1) below, and is generally performed in the form of a mixture of ethylbenzene gas and water vapor (steam) under elevated temperature.

$$C_6H_5.C_2H_5 \rightarrow C_6H_5.C_2H_3 + H_2 - 113 \text{ kJ/mol} \qquad (1)$$

Typically, the operation is performed with the inlet temperature of a catalyst bed being maintained to 600° C. to 650° C., although the temperature depends on the reactor and reaction conditions.

Such a method for producing styrene monomer has become technically feasible by virtue of the finding that iron oxide-potassium oxide catalysts (Fe—K catalysts) are less likely to be poisoned by steam, and consistently maintain a high performance. However, the catalyst needs to have a wider variety of performances according to the growing needs mentioned above.

The following are examples of important performance requirements for a catalyst for dehydrogenating ethylbenzene:
1) as low an operation temperature as possible;
2) high production yield of styrene;
3) low degree of catalyst deactivation due to, for example, carbon deposit;
4) the shaped product of the catalyst having sufficient mechanical strength to withstand stress during reaction; and
5) low production cost.

The production yield of styrene is calculated as the product of the conversion and the selectivity.

The Fe—K catalyst described above is characterised in that it meets the performance requirements 1) as low an operation temperature as possible and 2) high production yield of styrene, and it is widely known that a composite oxide ($KFeO_2$), generated from the reaction of Fe—K, which functions as an active species provides such features. With regard to lowering the activity due to carbon deposition in relation to 3), it is believed that potassium oxide maintains the activity through the facilitation of water gas shift reactions between the carbonaceous substance deposited on the surface of the catalyst and steam. Attempts to add an additional element to the Fe—K system to further improve its performance with respect to 1) and 2) above have been made, and, for example, the addition of an element such as Ce, Mo, Ca, Mg, Cr or the like to the Fe—K system is considered to be preferable for improvement of the activity (Patent Literature 1). Furthermore, improvements to the method for producing a catalyst, for example, improving the method for doping the third and fourth components to be added to iron oxide, have been attempted to improve the selectivity of a catalyst as much as possible (Patent Literature 2).

When a catalyst is shaped into pellets or the like and then installed in a reaction apparatus, the pellets are deformed by high temperature/high pressure stress applied to the catalyst in reaction, and interrupt the flow of reaction gas or the like to result in the suspension of the operation in the worst-case scenario. It is known that, to obtain the mechanical strength required to withstand the stress, the use of cerium carbonate hydroxide or a mixture of cerium carbonate hydroxide and cerium carbonate as a cerium raw material is particularly preferred (Patent Literature 3).

For the reason as described above, the development of a catalyst material has been heretofore conducted with the focus on the Fe—K—Ce system, and further improvement has been made through the addition of an element such as Mo and Ca, as described above, and as a result the Fe—K—Ce system has become widely used in the production process for styrene. However, the market is strongly demanding a lower cost and environmental friendliness, and thus further improved catalysts are required. One goal of such an improvement is the achievement of further reduced energy consumption and higher yield based on 1) and 2) above, without impairing 3) and 4) above.

In relation to the fact that the dehydrogenation of ethylbenzene is an endothermic reaction, there is a high demand for feature 1). The reason for this is that the outlet temperature of a catalyst bed in an actual reactor for production of styrene is under the inlet temperature by approximately 50 to 100° C., although the difference depends on reaction conditions, and thus maintenance of high activity not only at the inlet temperature of the catalyst bed (e.g. 600 to 650° C.) but also at the lower outlet temperature of the catalyst bed (e.g. under 600° C.) leads to a high yield on the whole of the reactor.

In Patent Literature 2, an improved yield is achieved through the improvement of the selectivity by adding third and fourth elements. However, no reference is made to the activity in a low-temperature region expected in the outlet of a reactor, and in Examples the reaction temperature is rather elevated on purpose to achieve a conversion of 70%, and the activity at low temperatures is not clear. Thus, whether the yield on the whole of an actual reactor is high is unclear.

For another example of attempts to improve the performance of a catalyst by adding third and fourth elements thereto, Patent Literature 4 demonstrates that additions of less than 300 ppm of Ti to an Fe—K—Ce material prevents the catalyst from being deactivated, and this allows the achievement of a conversion through a smaller rise in the reaction temperature. Even in Patent Literature 4, however, no reference is made to the activity in a low-temperature region expected in the outlet of a reactor, and in Examples the reaction temperature is rather elevated on purpose to achieve a conversion of 70%, and the activity at low temperatures is not clear.

Even in the case that adding third and fourth elements, as shown in Patent Literature 2 and Patent Literature 4, is found to improve the activity, other properties, for example, the mechanical strength of the catalyst may deteriorate depending on the type and quantity of the element added, and adequate care is needed to improve productivity in a practical way.

Although catalysts for dehydrogenizing ethylbenzene which cause less carbon deposits in reaction and provide a high yield in a high-temperature region have been heretofore proposed as described above, no catalyst which exhibits high activity even in a low-temperature region corresponding to the outlet temperature of a catalyst bed in an actual reactor and provides a high yield on the whole of a reactor has been proposed yet.

CITATION LIST

Patent Literature

Patent Literature 1: U.S. Pat. No. 5,023,225B
Patent Literature 2: JP4259612B
Patent Literature 3: JP5096751B
Patent Literature 4: JP5102626B

SUMMARY OF INVENTION

Technical Problem

An object of the present invention is to provide a catalyst which is highly active in the dehydrogenation reaction of an alkylaromatic hydrocarbon in the presence of steam not only in high-temperature regions (e.g. 600 to 650° C.) as found in the inlet of a catalyst bed in an apparatus for the production of SM but also in low-temperature regions (e.g. under 600° C.) as found in the outlet of a catalyst bed, where the temperature decreases as a result of the endothermic reaction; a process for producing the catalyst; and a dehydrogenation process using the catalyst.

Another object of the present invention is to provide a catalyst which undergoes less activity reduction even after long, continuous use for dehydrogenation, and thus provides a high reaction yield; and a process for producing the catalyst.

A further object of the present invention is to provide a catalyst having a smaller variation in reaction yield even when the temperature in the reaction apparatus changes in the dehydrogenation reaction of an alkylaromatic hydrocarbon.

Still another object of the present invention is to provide a catalyst having higher catalytic performance than conventional pellets of dehydrogenation catalysts without lowering the mechanical strength thereof.

Other objects of the present invention will become clear from the following description.

Solution to the Problem

In view of the circumstances described above, the inventors researched thoroughly to overcome the drawbacks of conventional arts, and consequently reached the following guidelines and results as possible solutions to the problem of the present invention.

(1) In order to find a catalyst which exhibits high activity even in low-temperature regions while maintaining high selectivity and physical strength, a search for a fourth element component was conducted with the focus on the Fe—K—Ce system.

(2) The inventors searched for such a fourth element, with reference to those exemplified in such documents as Patent Literatures 2 and 4, and those described in other literature. In the methodology, the reaction temperature was purposely changed and the yield was measured. In addition, an element which undergoes no lowering of activity even after being subjected to a constant temperature for a long period was also sought after.

(3) The result demonstrated that there are several elements which undergo improvement of activity in high-temperature regions, like Ca and Mo described in Patent Literature 1 as mentioned above. However, it was extremely difficult to discover an element providing high activity even in low-temperature regions (e.g. under 600° C.).

(4) In such a situation, the inventors focused on elements considered preferable for improving the activity in Patent Literature 2 or Patent Literature 4, and each of the elements was added to the Fe—K—Ce system for evaluation. Surprisingly, it was found that, among many such elements, the addition of a rare earth element (other than Ce) provides a catalyst having high activity even in low-temperature regions. It was also found that the addition of a rare earth element does not degrade the selectivity.

(5) Furthermore, it was found that, among rare earth elements, Y, Dy and La are preferable, in particular Y and Dy.

(6) The dehydrogenation catalyst thus obtained was found to be better in all factors of increase in the activity in association with the initiation of reaction, the peak value of the activity, and maintenance of the activity after long-term reaction than conventional Fe—K—Ce catalysts, and in addition it was found that the dehydrogenation catalyst has the remarkable effect of providing extremely high productivity resulting from its high performance in low-temperature regions. Thus, the inventors achieved the present invention.

The reason for the improvement in activity particularly in low-temperature regions, as well as high-temperature regions, by allowing an Fe—K—Ce catalyst to further contain a rare earth element other than Ce, is not clear. In particular, the phenomenon of improvement in activity in low-temperature regions suggests that the difference between the activity in high-temperature regions and the activity in low-temperature regions is small. Considering the conversion as the reaction rate, the degree of temperature dependence thereof is understood to correspond to the amount of activation energy. The phenomenon of the degree of temperature dependence being lowered while achieving high reaction activity through the use of the rare earth element is expected to correspond to an increase in the frequency factor in the Arrhenius equation for a reaction rate.

Through the above process, the inventors reached the following invention.

1. An alkylaromatic compound dehydrogenation catalyst, comprising iron (Fe), potassium (K) and cerium (Ce), and at least one rare earth element other than cerium.
2. The catalyst according to the above 1, wherein the rare earth element is selected from the group consisting of yttrium (Y), lanthanum (La), scandium (Sc), samarium (Sm) and neodymium (Nd).
3. The catalyst according to the above 1 or 2, comprising iron in an amount of 30 to 90% by weight calculated as $Fe_2O_3$, potassium in an amount of 1 to 50% by weight calculated as $K_2O$, cerium in an amount of 1 to 50% by weight calculated as $CeO_2$ and the rare earth element in an amount of 0.01 to 10% by weight calculated as an oxide of the rare earth, relative to 100% by weight of the total amount of the catalyst.

4. The catalyst according to any one of the above 1 to 3, wherein the rare earth element is yttrium (Y).
5. The catalyst according to the above 4, comprising iron in an amount of 30 to 90% by weight calculated as $Fe_2O_3$, potassium in an amount of 1 to 50% by weight calculated as $K_2O$, cerium in an amount of 1 to 50% by weight calculated as $CeO_2$ and yttrium in an amount of 0.01 to 10% by weight calculated as $Y_2O_3$, relative to 100% by weight of the total amount of the catalyst.
6. The catalyst according to the above 4 or 5, wherein the amount of yttrium is 0.03 to 5% by weight calculated as $Y_2O_3$, relative to 100% by weight of the total amount of the catalyst.
7. The catalyst according to any one of the above 1 to 6, further comprising a Group 2 element and/or a Group 6 element.
8. The catalyst according to the above 7, comprising a Group 2 element and a Group 6 element, wherein the amount of the Group 2 element is 0.3 to 10% by weight calculated as an oxide of the Group 2 element relative to 100% by weight of the total amount of the catalyst, and the amount of the Group 6 element is 0.1 to 10% by weight calculated as an oxide of the Group 6 element relative to 100% by weight of the total amount of the catalyst.
9. The catalyst according to any one of the above 1 to 8, further comprising an alkali metal other than potassium.
10. The catalyst according to the above 9, comprising a Group 2 element, a Group 6 element and an alkali metal other than potassium.
11. The catalyst according to any one of the above 7, 8 and 10, wherein the Group 2 element is calcium (Ca) and the Group 6 element is molybdenum (Mo).
12. The catalyst according to the above 9 or 10, wherein the alkali metal other than potassium is sodium (Na).
13. The catalyst according to any one of the above 10 to 12, comprising calcium, molybdenum and sodium.
14. The catalyst according to the above 11 or 13, wherein the amount of calcium is 0.3 to 10% by weight calculated as CaO relative to 100% by weight of the total amount of the catalyst, and the amount of molybdenum is 0.1 to 10% by weight calculated as $MoO_3$ relative to 100% by weight of the total amount of the catalyst.
15. The catalyst according to any one of the above 1 to 14, further comprising a noble metal in an amount of 0.1 to 200 ppm by weight, wherein the noble metal is selected from the group consisting of platinum and palladium.
16. The catalyst according to any one of the above 1 to 15, for dehydrogenating an alkylaromatic compound by contacting an alkylaromatic compound with steam at an $H_2O$/alkylaromatic compound ratio (weight ratio) of 0.5 to 1.5 at an inlet temperature of 600° C. to 650° C. and an outlet temperature of under 600° C.
17. A process for producing an alkenylaromatic compound, comprising a step of contacting an alkylaromatic compound with steam in the presence of the catalyst according to any one of the above 1 to 15.
18. The process according to the above 17, wherein the alkylaromatic compound is contacted with steam at an $H_2O$/alkylaromatic compound ratio (weight ratio) of 0.5 to 1.5.
19. The process according to the above 17 or 18, wherein the alkylaromatic compound is contacted with steam at an inlet temperature of 600° C. to 650° C. and an outlet temperature of under 600° C.
20. The process according to any one of the above 17 to 19, wherein the alkylaromatic compound is ethylbenzene and the alkenylaromatic compound is styrene.

21. A process for producing an alkylaromatic compound dehydrogenation catalyst, comprising the steps of:
   (i) mixing a raw material for the catalyst with water in an amount sufficient to produce an extrudable mixture, to prepare an extrudable mixture;
   (ii) forming the extrudable mixture obtained in step (i) into a pellet; and
   (iii) drying and then calcining the pellet obtained in step (ii) to obtain a finished catalyst,
   wherein the raw material for the catalyst comprises an iron compound, a potassium compound, a cerium compound and a compound of a rare earth other than cerium.
22. The process according to the above 21, wherein the rare earth other than cerium comprises an element selected from the group consisting of yttrium (Y), lanthanum (La), scandium (Sc), samarium (Sm) and neodymium (Nd).

In addition, the present invention encompasses the following embodiments.
1. An alkylaromatic compound dehydrogenation catalyst, comprising iron (Fe), potassium (K) and cerium (Ce), and at least one rare earth element other than cerium.
2. The catalyst according to the above 1, wherein the rare earth element is selected from the group consisting of yttrium (Y), lanthanum (La), scandium (Sc), samarium (Sm), dysprosium (Dy), terbium (Tb) and neodymium (Nd).
3. The catalyst according to the above 1 or 2, comprising iron in an amount of 30 to 90% by weight calculated as $Fe_2O_3$, potassium in an amount of 1 to 50% by weight calculated as $K_2O$, cerium in an amount of 1 to 50% by weight calculated as $CeO_2$ and the rare earth element in an amount of 0.01 to 10% by weight calculated as an oxide of the rare earth, relative to 100% by weight of the total amount of the catalyst.
4. The catalyst according to any one of the above 1 to 3, wherein the rare earth element is yttrium (Y).
5. The catalyst according to any one of the above 1 to 3, wherein the rare earth element is dysprosium (Dy).
6. The catalyst according to the above 4, comprising iron in an amount of 30 to 90% by weight calculated as $Fe_2O_3$, potassium in an amount of 1 to 50% by weight calculated as $K_2O$, cerium in an amount of 1 to 50% by weight calculated as $CeO_2$ and yttrium in an amount of 0.01 to 10% by weight calculated as $Y_2O_3$, relative to 100% by weight of the total amount of the catalyst.
7. The catalyst according to the above 4 or 6, wherein the amount of yttrium is 0.03 to 5% by weight calculated as $Y_2O_3$, relative to 100% by weight of the total amount of the catalyst.
8. The catalyst according to the above 5, comprising iron in an amount of 30 to 90% by weight calculated as $Fe_2O_3$, potassium in an amount of 1 to 50% by weight calculated as $K_2O$, cerium in an amount of 1 to 50% by weight calculated as $CeO_2$ and dysprosium in an amount of 0.01 to 10% by weight calculated as $Dy_2O_3$, relative to 100% by weight of the total amount of the catalyst.
9. The catalyst according to the above 5 or 8, wherein the amount of dysprosium is 0.03 to 5% by weight calculated as $Dy_2O_3$, relative to 100% by weight of the total amount of the catalyst.
10. The catalyst according to any one of the above 1 to 9, further comprising a Group 2 element and/or a Group 6 element.
11. The catalyst according to the above 10, comprising a Group 2 element and a Group 6 element, wherein the amount of the Group 2 element is 0.3 to 10% by weight calculated as an oxide of the Group 2 element relative to 100% by weight of the total amount of the catalyst, and the amount of the Group 6 element is 0.1 to 10% by weight calculated as an oxide of the Group 6 element relative to 100% by weight of the total amount of the catalyst.

12. The catalyst according to any one of the above 1 to 11, further comprising an alkali metal other than potassium.
13. The catalyst according to the above 12, comprising a Group 2 element, a Group 6 element and an alkali metal other than potassium.
14. The catalyst according to any one of the above 10, 11 and 13, wherein the Group 2 element is calcium (Ca) and the Group 6 element is molybdenum (Mo).
15. The catalyst according to the above 12 or 13, wherein the alkali metal other than potassium is sodium (Na).
16. The catalyst according to any one of the above 13 to 15, comprising calcium, molybdenum and sodium.
17. The catalyst according to the above 14 or 16, wherein the amount of calcium is 0.3 to 10% by weight calculated as CaO relative to 100% by weight of the total amount of the catalyst, and the amount of molybdenum is 0.1 to 10% by weight calculated as $MoO_3$ relative to 100% by weight of the total amount of the catalyst.
18. The catalyst according to any one of the above 1 to 17, further comprising a noble metal in an amount of 0.1 to 200 ppm by weight, wherein the noble metal is selected from the group consisting of platinum and palladium.
19. The catalyst according to any one of the above 1 to 18, for dehydrogenating an alkylaromatic compound by contacting an alkylaromatic compound with steam at an $H_2O$/alkylaromatic compound ratio (weight ratio) of 0.5 to 1.5 at an inlet temperature of 600° C. to 650° C. and an outlet temperature of under 600° C.
20. A process for producing an alkenylaromatic compound, comprising a step of contacting an alkylaromatic compound with steam in the presence of the catalyst according to any one of the above 1 to 18.
21. The process according to the above 20, wherein the alkylaromatic compound is contacted with steam at an $H_2O$/alkylaromatic compound ratio (weight ratio) of 0.5 to 1.5.
22. The process according to the above 20 or 21, wherein the alkylaromatic compound is contacted with steam at an inlet temperature of 600° C. to 650° C. and an outlet temperature of under 600° C.
23. The process according to any one of the above 20 to 22, wherein the alkylaromatic compound is ethylbenzene and the alkenylaromatic compound is styrene.
24. A process for producing an alkylaromatic compound dehydrogenation catalyst, comprising the steps of:
(i) mixing a raw material for the catalyst with water in an amount sufficient to produce an extrudable mixture, to prepare an extrudable mixture;
(ii) forming the extrudable mixture obtained in step (i) into a pellet; and
(iii) drying and then calcining the pellet obtained in step (ii) to obtain a finished catalyst,
wherein the raw material for the catalyst comprises an iron compound, a potassium compound, a cerium compound and a compound of a rare earth other than cerium.
25. The process according to the above 24, wherein the rare earth other than cerium comprises an element selected from the group consisting of yttrium (Y), lanthanum (La), scandium (Sc), samarium (Sm), dysprosium (Dy), terbium (Tb) and neodymium (Nd).
26. The catalyst according to any one of the above 3 to 5, further comprising an alkali metal other than potassium, wherein the alkali metal is sodium (Na).
27. The catalyst according to the above 26, comprising sodium in an amount of 0.001 to 15% by weight calculated as $Na_2O$ relative to 100% by weight of the total amount of the catalyst.
28. The catalyst according to any one of the above 6 to 11, further comprising an alkali metal other than potassium, wherein the alkali metal is sodium (Na).
29. The catalyst according to the above 28, comprising sodium in an amount of 0.001 to 15% by weight calculated as $Na_2O$ relative to 100% by weight of the total amount of the catalyst.

DESCRIPTION OF THE INVENTION

What follows is a detailed description of the present invention.

The alkylaromatic compound dehydrogenation catalyst (a catalyst for dehydrogenation of an alkyl group in an alkylaromatic compound) according to the present invention contains iron. In an embodiment of the present invention, the catalyst can contain iron in the form of an iron compound, for example, an oxide or composite oxide of iron. Here, "composite oxide" refers to an oxide containing two or more non-oxygen atoms in the structure of the corresponding oxide.

The catalyst can contain iron in an amount of 30 to 90% by weight, preferably in an amount of 40 to 85% by weight, more preferably in an amount of 50 to 80% by weight, for example, in an amount of 60 to 80% by weight or 70 to 80% by weight, calculated as $Fe_2O_3$, based on the total weight of the catalyst.

For a raw material iron (i.e. an iron source), an iron compound such as iron oxide can be used, and potassium ferrite (a composite oxide of iron and potassium) and sodium ferrite (a composite oxide of iron and sodium) and the like can be also used but iron oxide is preferable.

For the iron oxide used in the present invention, different forms of iron oxide such as red, yellow, brown and black iron oxides can be used. However, red iron oxide (hematite, $Fe_2O_3$) is preferable, and several types of iron oxide may be used in admixture with one another, such as yellow iron oxide (goethite, $Fe_2O_3 \cdot H_2O$) and red iron oxide used in admixture with each other.

The raw material iron can be e.g. red iron oxide, or yellow iron oxide as a precursor compound of red iron oxide.

The catalyst contains potassium. In an embodiment of the present invention, the catalyst can contain potassium in the form of a potassium compound, for example, an oxide or composite oxide of potassium.

The catalyst can contain potassium in an amount of 1 to 50% by weight, preferably in an amount of 5 to 30% by weight, more preferably in an amount of 10 to 20% by weight, for example, in an amount of 10 to 15% by weight, calculated as $K_2O$, based on the total weight of the catalyst.

For a raw material potassium (i.e. a potassium source), any compound which provides a potassium compound (e.g. an oxide or composite oxide of potassium) after calcination can be used. However, compounds which do not leave a component having a poisoning effect on the catalyst are preferable. Typically, potassium hydroxide, potassium carbonate or the like is used.

For the raw material to be used, potassium compounds including oxides, hydroxides, carbonates and bicarbonates, and mixtures of two or more thereof are preferable, and potassium carbonate or a mixture of potassium carbonate and potassium hydroxide is particularly preferable. In one preferred embodiment of the present invention, potassium carbonate is used as a raw material for potassium.

The catalyst further contains cerium. In an embodiment of the present invention, the catalyst can contain cerium in the form of a cerium compound, for example, an oxide or composite oxide of cerium.

The catalyst can contain cerium in an amount of 1 to 50% by weight, preferably in an amount of 3 to 40% by weight, more preferably in an amount of 5 to 20% by weight, for example, in an amount of 5 to 15% by weight or 5 to 10% by weight, calculated as $CeO_2$, based on the total weight of the catalyst.

For a raw material cerium (i.e. a cerium source), any compound which provides a cerium compound (e.g. an oxide or composite oxide of cerium) after calcination can be used. However, compounds which do not leave a component having a poisoning effect on the catalyst are preferable.

For a raw material for cerium, for example, cerium carbonate hydroxide or a mixture of cerium carbonate hydroxide and another cerium compound is preferable. Examples of other preferred cerium raw materials include cerium compounds such as cerium oxide, cerium hydroxide, cerium carbonate and cerium nitrate, and mixtures of two or more thereof. In one preferred embodiment of the present invention, cerium carbonate is used as a raw material for cerium. Cerium carbonate may be a hydrate thereof, and in this case the cerium content in cerium carbonate hydrate is preferably 40% or more, and more preferably 50% or more, calculated as the weight of $CeO_2$.

In the case that cerium carbonate hydroxide is used in the present invention, the cerium carbonate hydroxide is characterised in that its cerium content based on the oxide is 50% or more, preferably 60% or more, and more preferably 65% or more, and its particle size is 0.1 to 30 μm, and preferably 0.5 to 5 μm.

The cerium carbonate hydroxide (cerium carbonate hydroxide, $CeCO_3OH$ or cerium carbonate hydroxide hydrate, $Ce_2(CO_3)_2(OH)_2 \cdot H_2O$) is also called basic cerium carbonate, cerium hydroxycarbonate, etc. In addition, the cerium carbonate hydroxide is occasionally represented by the name and chemical formula of cerium oxide carbonate hydrate $(Ce(CO_3)_2O \cdot H_2O$ or $Ce_2O(CO_3)_2 \cdot H_2O$ or $CeO(CO_3)_2 \cdot xH_2O)$. Hence, the name and chemical formula do not matter as long as the compound has a feature similar to the feature mentioned above.

In addition to iron, potassium and cerium, the catalyst according to the present invention contains at least one rare earth element other than cerium.

Said at least one rare earth element is, for example, selected from the group consisting of yttrium (Y), lanthanum (La), scandium (Sc), samarium (Sm), dysprosium (Dy), terbium (Tb), neodymium (Nd), and a combination of two or more thereof. The at least one rare earth element is preferably yttrium, lanthanum or dysprosium, and particularly preferably yttrium or dysprosium.

In an embodiment of the present invention, the catalyst according to the present invention can contain a rare earth element other than cerium (hereinafter, also referred to as "rare earth element" or "rare earth", simply) in the form of a compound of a rare earth, for example, an oxide or composite oxide of a rare earth element.

The catalyst can contain said rare earth element in an amount of 0.01 to 10% by weight, for example, in an amount of 0.01% by weight or more and less than 10% by weight, calculated as the oxide thereof, based on the total weight of the catalyst. The catalyst can contain the rare earth element preferably in an amount of 0.03 to 5% by weight, more preferably in an amount of 0.05 to 3% by weight, even more preferably in an amount of 0.1 to 2% by weight, for example, in an amount of 0.3 to 1% by weight or 0.3 to 0.8% by weight, calculated as the oxide thereof, based on the total weight of the catalyst.

For a raw material for the rare earth element (i.e. a source of said rare earth element), any compound providing a compound of the rare earth (e.g. an oxide or composite oxide of the rare earth element) after calcination can be used. A compound, for example, an oxide, hydroxide, carbonate, nitrate, phosphate, sulfate, acetate, chloride or sulfide of the rare earth element, or a mixture of two or more thereof can be used, for example.

In an embodiment of the present invention, the catalyst contains yttrium, in addition to iron, potassium and cerium. The yttrium can be present in a form of a compound, for example, an oxide or composite oxide thereof.

The catalyst can contain yttrium in an amount of 0.01 to 10% by weight, for example, in an amount of 0.01% by weight or more and less than 10% by weight, calculated as $Y_2O_3$, based on the total weight of the catalyst. The catalyst can contain yttrium preferably in an amount of 0.03 to 5% by weight, more preferably in an amount of 0.05 to 3% by weight, even more preferably in an amount of 0.1 to 2% by weight, for example, in an amount of 0.3 to 1% by weight or 0.3 to 0.8% by weight, calculated as $Y_2O_3$, based on the total weight of the catalyst.

In the present invention, it was further found that the effect described above (exertion of high catalytic performance even in low-temperature regions) can be achieved even at such a low yttrium content.

For a raw material yttrium (i.e. an yttrium source), any compound which provides an yttrium compound (e.g. an oxide or composite oxide of yttrium) after calcination can be used. A compound, for example, an oxide, hydroxide, carbonate, nitrate, phosphate, sulfate, acetate, chloride or sulfide of yttrium, or a mixture of two or more thereof can be used. In the case that a nitrate is used, the nitrate can be a hydrate, for example, a hexahydrate thereof. Preferably, yttrium oxide or yttrium nitrate (e.g. yttrium nitrate hexahydrate) is used as a raw material.

In a further embodiment of the present invention, the catalyst contains lanthanum, in addition to iron, potassium and cerium. The lanthanum can be present in a form of a compound, for example, an oxide or composite oxide thereof.

The catalyst can contain lanthanum in an amount of 0.01 to 10% by weight, for example, 0.01% by weight or more and less than 10% by weight, calculated as $La_2O_3$, based on the total weight of the catalyst. The catalyst can contain lanthanum preferably in an amount of 0.03 to 5% by weight, more preferably in an amount of 0.05 to 3% by weight, even more preferably in an amount of 0.1 to 2% by weight, for example, in an amount of 0.3 to 1% by weight or 0.3 to 0.8% by weight, calculated as $La_2O_3$, based on the total weight of the catalyst.

In the present invention, the effect described above (exertion of high catalytic performance even in low-temperature regions) can be achieved even at such a low lanthanum content.

For a raw material lanthanum (i.e. a lanthanum source), any compound which provides a lanthanum compound (e.g. an oxide or composite oxide of lanthanum) after calcination can be used. A compound, for example, an oxide, hydroxide, carbonate, nitrate, phosphate, sulfate, acetate, chloride or sulfide of lanthanum, or a mixture of two or more thereof can be used. Preferably, lanthanum oxide is used as a raw material.

In still another embodiment of the present invention, the catalyst contains dysprosium, in addition to iron, potassium and cerium. The dysprosium can be present in a form of a compound, for example, an oxide or composite oxide thereof.

The catalyst can contain dysprosium in an amount of 0.01 to 10% by weight, for example, in an amount of 0.01% by weight or more and less than 10% by weight, calculated as $Dy_2O_3$, based on the total weight of the catalyst. The catalyst can contain dysprosium preferably in an amount of 0.03 to 5% by weight, more preferably in an amount of 0.05 to 3% by weight, even more preferably in an amount of 0.1 to 2% by weight, for example, in an amount of 0.3 to 1% by weight or 0.3 to 0.8% by weight, calculated as $Dy_2O_3$, based on the total weight of the catalyst.

In the present invention, it was further found that the effect described above (exertion of high catalytic performance even in low-temperature regions) can be achieved even at such a low dysprosium content.

For a raw material dysprosium (i.e. a dysprosium source), any compound providing a dysprosium compound (e.g. an oxide or composite oxide of dysprosium) after calcination can be used. A compound, for example, an oxide, hydroxide, carbonate, nitrate, phosphate, sulfate, acetate, chloride or sulfide of dysprosium, or a mixture of two or more thereof can be used. In the case that a nitrate is used, the nitrate can be a hydrate, for example, a pentahydrate or hexahydrate thereof. Preferably, dysprosium oxide or dysprosium nitrate (e.g. dysprosium nitrate pentahydrate) is used as a raw material.

In an embodiment of the present invention, the content of each catalyst component in the present invention is in the following range represented calculated as the oxide, based on the total weight of the catalyst.

$Fe_2O_3$ 30.0 to 90.0% by weight
$K_2O$ 1.0 to 50.0% by weight
$CeO_2$ 1.0 to 50.0% by weight
Oxide of rare earth other than Ce 0.01 to 10% by weight.

In an embodiment of the present invention, the mole ratio, iron:potassium:cerium:at least one rare earth element other than cerium, can be, for example, in the range of 1 to 1000:1 to 500:1 to 200:1, and preferably in the range of 1 to 300:1 to 100:1 to 50:1.

In an embodiment of the present invention, the catalyst substantially consists only of an iron compound, a potassium compound, a cerium compound and a compound of a rare earth other than cerium. In an embodiment of the present invention, the catalyst substantially consists only of an iron compound, a potassium compound, a cerium compound, and an yttrium compound and/or a lanthanum compound and/or a dysprosium compound.

In an embodiment of the present invention, the catalyst can further contain an additional cocatalyst. Here, the cocatalyst is defined as a component other than the base of the catalyst and which is not iron, potassium or cerium, and assists or reinforces the catalytic activity of the base of the catalyst.

Examples of such a cocatalyst component include Group 2 elements (e.g. magnesium, calcium) and Group 6 elements (e.g. molybdenum, tungsten).

Further examples of such a cocatalyst include titanium, zirconium, niobium, manganese, rhenium, cobalt, nickel, copper, zinc, boron, aluminum, gallium, indium, silicon, germanium, tin, phosphorus, antimony and bismuth. They are preferably contained in the catalyst in the form of a compound thereof (e.g. an oxide or composite oxide thereof).

In an embodiment of the present invention, the catalyst according to the present invention contains one of the above cocatalyst components, or combination of two or more thereof. The cocatalyst component is preferably one or more elements selected from the group consisting of molybdenum, calcium and magnesium, and for example, the cocatalyst component is molybdenum and/or calcium. In an embodiment of the present invention, each of the cocatalysts is contained in an amount of 0.0001 to 6.0% by weight, preferably in an amount of 0.001 to 5.0% by weight, for example, in an amount of 0.01 to 3.0% by weight, calculated as the oxide thereof, based on the total weight of the catalyst.

In an embodiment of the present invention, the catalyst according to the present invention contains molybdenum as the cocatalyst component in an amount of 0.001 to 15% by weight, preferably in an amount of 0.01 to 10% by weight, for example, in an amount of 0.05 to 1% by weight, more preferably in an amount of 0.1 to 0.5% by weight, calculated as $MoO_3$, based on the total weight of the catalyst.

In an embodiment of the present invention, the catalyst according to the present invention contains calcium as the cocatalyst component in an amount of 0.001 to 15% by weight, preferably in an amount of 0.01 to 10% by weight, for example, in an amount of 0.05 to 5% by weight, more preferably in an amount of 0.3 to 3% by weight, even more preferably in an amount of 0.5 to 2% by weight, calculated as CaO, based on the total weight of the catalyst.

In an embodiment of the present invention, the catalyst according to the present invention contains molybdenum and calcium, as the cocatalyst component, in a form of compounds thereof, for example, molybdenum oxide and calcium oxide. In this embodiment, the catalyst contains molybdenum in an amount of 0.001 to 15% by weight, preferably in an amount of 0.01 to 10% by weight, for example, in an amount of 0.05 to 1% by weight, more preferably in an amount of 0.1 to 0.5% by weight, calculated as $MoO_3$, based on the total weight of the catalyst, and contains calcium in an amount of 0.001 to 15% by weight, preferably in an amount of 0.01 to 10% by weight, for example, in an amount of 0.05 to 5% by weight, more preferably in an amount of 0.3 to 3% by weight, even more preferably in an amount of 0.5 to 2% by weight, calculated as CaO, based on the total weight of the catalyst.

The component added as the cocatalyst component is not necessarily an oxide, and any component which provides a compound (e.g. an oxide or composite oxide) of the component through heat treatment (e.g. calcination) can be used. However, those not containing any component serving as a catalyst poison are preferred. In the case where the catalyst contains molybdenum and/or calcium as the cocatalyst component, for example, molybdenum oxide and calcium hydroxide can be used as raw materials for the components.

The catalyst according to the present invention can contain a noble metal. Examples of the noble metal include gold, silver, platinum, palladium, rhodium, iridium, ruthenium and osmium, and preferred are platinum and palladium.

The noble metal source is not limited. In the case that the noble metal is palladium, for example, palladium nitrate can be used.

The catalyst can contain the noble metal, for example, in an amount of 0.1 to 200 ppm by weight, preferably in an amount of 1 to 100 ppm by weight, more preferably in an amount of 10 to 50 ppm by weight, for example, in an amount of 10 to 30 ppm by weight, based on the total weight of the catalyst.

The catalyst according to the present invention can further contain an additional alkali metal in addition to potassium. In an embodiment of the present invention, the catalyst can contain one or more elements selected from the group consisting of a Group 2 element, a Group 6 element and an alkali metal other than potassium. For example, the catalyst can contain a Group 2 element, a Group 6 element and an alkali metal other than potassium.

For the additional alkali metal, for example, sodium is preferable. The catalyst according to the present invention can contain the additional alkali metal (preferably, sodium) in the form of an alkali metal compound (preferably, a sodium compound), for example, an oxide or composite oxide of an alkali metal (preferably, an oxide or composite oxide of sodium).

In an embodiment of the present invention, the catalyst according to the present invention can contain one or more elements selected from the group consisting of calcium, molybdenum and sodium. For example, the catalyst can contain calcium, molybdenum and sodium.

In an embodiment of the present invention, the catalyst according to the present invention contains sodium in an amount of 0.001 to 15% by weight, preferably in an amount of 0.01 to 10% by weight, for example, in an amount of 0.05 to 5% by weight, more preferably in an amount of 0.5 to 5% by weight, for example, in an amount of 1 to 3% by weight, calculated as $Na_2O$, based on the total weight of the catalyst.

For a raw material sodium (i.e. a sodium source), any compound which provides a sodium compound (e.g. an oxide or composite oxide of sodium) after calcination can be used. Preferably, sodium carbonate is used.

The contents of iron, potassium, cerium, a rare earth element other than cerium and other elements, and mole ratio among the elements in the catalyst can be determined by using a method known to those skilled in the art, such as elemental analysis with fluorescent X-ray analysis (XRF analysis). For example, the model ZSX Primus II manufactured by Rigaku Corporation can be used for the measurement. First, a measurement sample is ground and then pressed at 20 MPa to prepare a test sheet approximately 3 mm thick. Subsequently, the resulting test sheet is subjected to XRF analysis. A calibration curve is separately prepared from the result of the XRF analysis for a standard substance containing an element to be measured, and quantitative calculation is performed with reference to the calibration curve. The quantity of each element thus measured can be appropriately converted to the quantity calculated as the corresponding oxide (e.g. $Fe_2O_3$, $K_2O$), or converted to moles, to determine the aforementioned contents and mole ratio.

As is clear from the above description, the catalyst according to the present invention, in one embodiment of the present invention, can be a catalyst in the form of a metal oxide.

In the catalyst according to the present invention, the composition for components other than the components described above may be any composition, provided that it does not deteriorate the advantageous effects of the present invention. The catalyst according to the present invention may contain any substance other than the components described above, provided that the substance does not deteriorate the advantageous effects of the present invention; and for example, the catalyst may contain a binder, silica, etc.

In an embodiment of the present invention, the catalyst can substantially consist only of an iron compound, a potassium compound, a cerium compound and a compound of a rare earth other than cerium, and one or more compounds selected from the group consisting of a Group 2 element compound, a Group 6 element compound, a compound of an alkali metal other than potassium and a noble metal compound.

That is, in one embodiment of the present invention, the catalyst can contain only an iron compound, a potassium compound, a cerium compound and a compound of a rare earth other than cerium, and one or more compounds selected from the group consisting of a Group 2 element compound, a Group 6 element compound, a compound of an alkali metal other than potassium and a noble metal compound, as catalyst components or cocatalyst components.

In another embodiment of the present invention, the catalyst does not contain chromium (Cr).

The catalyst according to the present invention can be produced in accordance with a method known in the art for catalyst production. To produce the catalyst according to the present invention, for example, raw materials for the catalyst are mixed together and subjected to shape forming to give a shaped article, and the shaped article is dried and calcined.

The shape of the shaped article is not limited, and the shaped article can be, for example, a granule, pellet, or cylindrical shaped article, for example, with a particle size of 0.1 mm to 10 mm, more preferably, with a particle size of approximately 0.2 to 7 mm.

In an embodiment of the present invention, the shaped article is a pellet. For the shape forming method, a known shape forming method can be used. When a pellet is produced, raw materials for the catalyst can be mixed together through wet kneading, and then subjected to extrusion.

The amount of water to be added in kneading is required to be suitable for subsequent extrusion, and the amount depends on the type of raw materials used. Typically, water in an amount in the range of 2 to 50% by weight is added, and the resultant is sufficiently kneaded, and then subjected to extrusion followed by drying and calcining, and thus a desired pellet of the dehydrogenation catalyst can be obtained. In drying, it is only required to remove free water contained in the extrudate, and drying is performed usually at a temperature of 60 to 200° C., preferably at a temperature of 70 to 150° C., for example, for 5 minutes to 5 hours, preferably for 15 minutes to 2 hours. Calcination is performed to improve the physical stability of the pellet of the catalyst and improve its performance through thermal decomposition of the catalyst precursors contained in the dried product, and performed usually in a temperature range of 400 to 1000° C., preferably in a temperature range of 500 to 950° C. For example, the calcination can be performed under normal pressure, for example, for 30 minutes to 10 hours, preferably for 1 to 5 hours.

Accordingly, in one aspect of the present invention, the present invention relates to a process for producing the above catalyst, comprising the steps of:

(i) mixing a raw material for the catalyst with water in an amount sufficient to produce an extrudable mixture, to prepare an extrudable mixture;

(ii) forming the extrudable mixture obtained in step (i) into a pellet; and (iii) drying and then calcining the pellet obtained in step (ii) to obtain a finished catalyst.

In another aspect of the present invention, the present invention relates to an alkylaromatic compound dehydrogenation catalyst produced by a process comprising the steps of:

(i) mixing a raw material for the catalyst with water in an amount sufficient to produce an extrudable mixture, to prepare an extrudable mixture;

(ii) forming the extrudable mixture obtained in step (i) into a pellet; and (iii) drying and then calcining the pellet obtained in step (ii) to obtain a finished catalyst.

The raw material for the catalyst comprises iron, potassium, cerium and at least one rare earth element other than cerium, and preferably contains an iron compound, a potassium compound, a cerium compound and a compound of a rare earth other than cerium. For example, the raw material for the catalyst can contain iron in the form of its oxide; potassium in the form of its oxide, hydroxide, carbonate or bicarbonate, or a mixture of two or more thereof; cerium in the form of its oxide, hydroxide, carbonate, nitrate, carbonate hydroxide, or a mixture of two or more thereof; and a rare earth other than cerium in a form of its oxide, hydroxide, carbonate, nitrate, phosphate, sulfate, acetate, chloride, sulfide, or a mixture of two or more thereof.

In an embodiment of the present invention, the raw material for the catalyst can contain iron oxide, potassium carbonate and cerium carbonate, and a compound selected from the group consisting of yttrium oxide, yttrium nitrate hexahydrate, lanthanum oxide, dysprosium oxide and dysprosium nitrate pentahydrate.

In an embodiment of the present invention, the raw material for the catalyst substantially consists only of an iron compound, a potassium compound, a cerium compound and a compound of a rare earth other than cerium.

In another embodiment of the present invention, the raw material for the catalyst can further contain an additional cocatalyst component preferably in a form of its compound. For example, the raw material for the catalyst can contain molybdenum oxide and/or calcium hydroxide.

Optionally, the raw material for the catalyst can further contain an alkali metal other than potassium and/or a noble metal, preferably in a form of a compound thereof, and for example, can contain sodium carbonate and/or palladium nitrate.

In still another embodiment of the present invention, the raw material for the catalyst substantially consists only of an iron compound, a potassium compound, a cerium compound and a compound of a rare earth other than cerium, and a compound selected from the group consisting of a Group 2 element compound, a Group 6 element compound, a compound of an alkali metal other than potassium and a noble metal compound.

That is, in one embodiment of the present invention, the raw material for the catalyst can contain only an iron compound, a potassium compound, a cerium compound and a compound of a rare earth other than cerium, and one or more compounds selected from the group consisting of a Group 2 element compound, a Group 6 element compound, a compound of an alkali metal other than potassium and a noble metal compound, as raw materials for catalyst components or cocatalyst components.

The dehydrogenation catalyst according to the present invention as described above, preferably a pellet consisting of the dehydrogenation catalyst composition as described above, has higher catalytic performance, without lowering the mechanical strength, than conventional dehydrogenation catalyst pellets, and is therefore suitable for industrial use.

The alkylaromatic compound dehydrogenation catalyst according to the present invention is effective as a dehydrogenation catalyst to generate an alkenylaromatic compound by contacting an alkylaromatic compound with steam, and in particular effective for promotion of dehydrogenation of ethylbenzene in production of styrene by contacting ethylbenzene with steam.

Here, the reaction conditions for dehydrogenation reaction may be any conditions commonly used for the reaction, and particularly not limited. The reaction can be performed by retaining contact between an alkylaromatic compound and steam in the presence of the catalyst according to the present invention at any pressure. The reaction is preferably performed at ambient pressure or reduced pressure, for example, at a pressure of 100 kPa or lower or 95 kPa or lower. On the other hand, the lower limit of pressure only depends on a reaction apparatus to be used, and is not limited, and it is generally adequate to perform the reaction at a pressure of 5 hPa to ambient pressure. In the reaction, an excessively high liquid hourly space velocity (LHSV) lowers the conversion of an alkylaromatic compound and thus a sufficient yield of an alkenylaromatic compound cannot be achieved, and an excessively low LHSV does not provide a sufficient yield. Hence, the LHSV is preferably in the range of 0.3 to 1.5, and more preferably in the range of 0.4 to 1.1.

In the present invention, it was found that use of the catalyst described above greatly improves the conversion of an alkylaromatic compound, preferably ethylbenzene, while the selectivity is kept high, not only in high-temperature regions but also in low-temperature regions. In addition, it was found that the catalyst increases the conversion in a wide temperature range, and in particular the increase in conversion in low-temperature regions can be even more remarkable than the increase in conversion in high-temperature regions.

Use of the catalyst according to the present invention enables the achievement of a high conversion while maintaining selectivity, even when the reaction is performed, for example, in the reaction zone of a reaction apparatus, typically a catalyst bed, with the inlet temperature at 600 to 660° C., preferably at 620 to 650° C. and the outlet temperature at under 600° C., preferably at 500 to 590° C., for example, at 520 to 580° C.

In the dehydrogenation reaction, a lower weight ratio (wt/wt) between steam and an alkylaromatic compound (preferably, ethylbenzene) (hereinafter, also referred to as "$H_2O$/alkylaromatic compound ratio") generally leads to a lower conversion. However, use of the catalyst according to the present invention enables the achievement of a high conversion while maintaining high selectivity even when the reaction is performed at a low $H_2O$/alkylaromatic compound ratio (e.g. at a low $H_2O$/ethylbenzene ratio). One reason therefore is presumably that the rare earth element other than cerium additionally contained inhibits the carbon deposition to a greater extent. Even at such a low $H_2O$/alkylaromatic compound ratio (e.g. at a low $H_2O$/ethylbenzene ratio), the present invention enables the achievement of a high conversion not only in high-temperature regions but also in low-temperature regions. Accordingly, use of the catalyst according to the present invention allows the setting of a low $H_2O$/alkylaromatic compound ratio, and thereby requiring a smaller quantity of heat.

Use of the catalyst according to the present invention enables achievement of a high conversion while maintaining selectivity even when the reaction is performed, for example, at an $H_2O$/alkylaromatic compound ratio (e.g. an $H_2O$/ethylbenzene ratio) of 0.2 to 1.8, preferably at an $H_2O$/alkylaromatic compound ratio of 0.5 to 1.5, for example, at an $H_2O$/alkylaromatic compound ratio of 0.8 to 1.2

Improvement of the conversion and reduction of necessary energy as described above are particularly important and useful for reaction on an industrial scale.

Accordingly, in one aspect of the present invention, the present invention relates to a process for producing an alkenylaromatic compound, the process comprising a step of contacting an alkylaromatic compound with steam in the presence of the catalyst described above, wherein, preferably, the alkylaromatic compound is ethylbenzene and the alkenylaromatic compound is styrene.

In a further aspect of the present invention, the present invention relates to a process for producing an alkenylaromatic compound, the process comprising a step of contacting an alkylaromatic compound with steam in the presence of the catalyst described above at an $H_2O$/alkylaromatic compound ratio (weight ratio) of 0.2 to 1.8, preferably at an $H_2O$/alkylaromatic compound ratio of 0.5 to 1.5, for example, at an $H_2O$/alkylaromatic compound ratio of 0.8 to 1.2. The alkylaromatic compound is preferably ethylbenzene and the alkenylaromatic compound is preferably styrene.

In a further aspect of the present invention, the present invention relates to a process for producing an alkenylaromatic compound, the process comprising a step of contacting an alkylaromatic compound with steam in the presence of the catalyst described above, for example, in the reaction zone of an alkenylaromatic compound production apparatus, typically in a catalyst bed, with the inlet temperature (the inlet temperature of a reaction zone, typically a catalyst bed) at 600 to 660° C., preferably at 620 to 650° C. and the outlet temperature (the outlet temperature of a reaction zone, typically a catalyst bed) at under 600° C., preferably at 500 to 590° C., for example, at 520 to 580° C. The alkylaromatic compound is preferably ethylbenzene and the alkenylaromatic compound is preferably styrene.

In another aspect of the present invention, the present invention relates to the catalyst described above for dehydrogenating an alkylaromatic compound by contacting an alkylaromatic compound with steam. Furthermore, the present invention relates to the catalyst described above for dehydrogenating an alkylaromatic compound through contacting an alkylaromatic compound with steam at an $H_2O$/alkylaromatic compound ratio (weight ratio) of 0.5 to 1.5 and/or at an inlet temperature of 600° C. to 650° C. and an outlet temperature of under 600° C. The alkylaromatic compound is preferably ethylbenzene and the alkenylaromatic compound is preferably styrene.

In still another aspect of the present invention, the present invention relates to a use of the catalyst described above for the production of an alkenylaromatic compound by contacting an alkylaromatic compound with steam. The alkylaromatic compound is preferably ethylbenzene and the alkenylaromatic compound is preferably styrene.

EXAMPLES

Hereinafter, the present invention will be specifically described with reference to Examples. However, the present invention is in no way limited to these Examples.

Comparative Example 1

800.0 g of red iron oxide (hematite crystal structure), 221.7 g of potassium carbonate and 211.4 g of cerium carbonate hydrate (containing 50% of cerium calculated as the weight of $CeO_2$) were weighed, and mixed together in a kneader while pure water was gradually added thereto to form a paste. The resulting paste mixture was shaped into cylindrical pellets 3 mm in diameter. The pellets were dried at 75° C. for 30 minutes, and then calcined at 900° C. for 2 hours.

Example 1

Preparation was performed in accordance with the method in Comparative Example 1 except that 5.3 g of yttrium oxide was added to the raw material.

The resulting catalysts were cut to a uniform length of to 4 mm to 6 mm. Said catalysts were used to initiate a reaction test under the following reaction conditions.

Amount of catalyst 100 cc
Liquid hourly space velocity (LHSV) of ethylbenzene as raw material=1.00 $h^{-1}$
(Flow rate of $H_2O$ for dilution)/(Flow rate of ethylbenzene as raw material)=1.00 wt/wt (weight ratio)
Reaction pressure=91 kPa (absolute pressure)
Reaction temperature=620° C.

After 200 hours of operation under the above reaction conditions, the reaction temperature was changed from 620° C. to 600° C., 570° C. or 540° C., and the products recovered from the reactor at the respective reaction temperatures were analysed, and the conversion of ethylbenzene (EB conversion) and the selectivity to styrene (SM selectivity) were determined by using the following equations.

EB conversion (% by weight)=(EB concentration (% by weight) in raw material solution−EB concentration (% by weight) in product solution)/EB concentration (% by weight) of raw material solution×100

SM selectivity (% by weight)=(SM concentration (% by weight) in product solution−SM concentration (% by weight) in raw material solution)/(EB concentration (% by weight) in raw material solution−EB concentration (% by weight) in product solution)×100

The conversion and selectivity in the case of using the calcined catalysts obtained in Comparative Example 1 and Example 1 are shown in Table 1.

TABLE 1

|  | Yttrium compound (form in adding) | EB conversion [%] at different reaction temperatures | | | | SM selectivity [%] at 50% EB conversion |
| --- | --- | --- | --- | --- | --- | --- |
|  |  | 620° C. | 600° C. | 570° C. | 540° C. |  |
| Comparative Example 1 | none | 63.9 | 51.9 | 37.2 | 17.9 | 96.65 |
| Example 1 | $Y_2O_3$ (powder) | 65.4 | 55.3 | 40.3 | 21.7 | 96.50 |

Comparative Example 2

778.5 g of red iron oxide (hematite crystal structure), 225.3 g of potassium carbonate, 214.8 g of cerium carbonate hydrate (containing 50% of cerium calculated as the weight of $CeO_2$), 36.7 g of sodium carbonate, 14.6 g of calcium hydroxide and 2.12 g of molybdenum oxide were weighed, and mixed together in a kneader while 15 cc of an aqueous solution of palladium nitrate containing 0.017 g of palladium was added thereto. Furthermore, pure water was gradually added thereto to form a paste, and the resulting mixture paste was shaped into cylindrical pellets 3 mm in diameter. The pellets were dried at 75° C. for 30 minutes, and then calcined at 900° C. for 2 hours.

Example 2

Preparation was performed in accordance with the method in Comparative Example 2 except that mixing was performed in a kneader while a solution containing 18.21 g of yttrium nitrate hexahydrate dissolved in 15 cc of pure water was added thereto.

Example 3

Preparation was performed in accordance with the method in Comparative Example 2 except that 5.4 g of yttrium oxide was added to the raw material.

Example 4

Preparation was performed in accordance with the method in Comparative Example 2 except that mixing was performed in a kneader while a solution containing 12.73 g of dysprosium nitrate pentahydrate dissolved in 15 cc of pure water was added thereto.

The catalytic performance for each of the calcined catalysts obtained in Comparative Example 2 and Examples 2 to 4 is shown in Table 2.

Comparative Example 3

Preparation was performed in accordance with the method in Comparative Example 2 except that 3.00 g of potassium metavanadate was added to the raw material.

Comparative Example 4

Preparation was performed in accordance with the method in Comparative Example 2 except that 10.71 g of tungsten trioxide was added to the raw material.

Comparative Example 5

Preparation was performed in accordance with the method in Comparative Example 2 except that 21.51 g of chromium oxide was added to the raw material.

Comparative Example 6

Preparation was performed in accordance with the method in Comparative Example 2 except that 31.18 g of basic copper carbonate was added to the raw material.

The resulting catalysts were cut to a uniform length of 4 mm to 6 mm. Said catalysts were used to initiate a reaction test under the following reaction conditions.

Amount of catalyst 100 cc

Liquid hourly space velocity (LHSV) of ethylbenzene as raw material=1.00 $h^{-1}$ (Flow rate of $H_2O$ for dilution)/(Flow rate of ethylbenzene as raw material)=1.00 wt/wt (weight ratio)

Reaction pressure=91 kPa (absolute pressure)

Reaction temperature=620° C.

Figure 1:
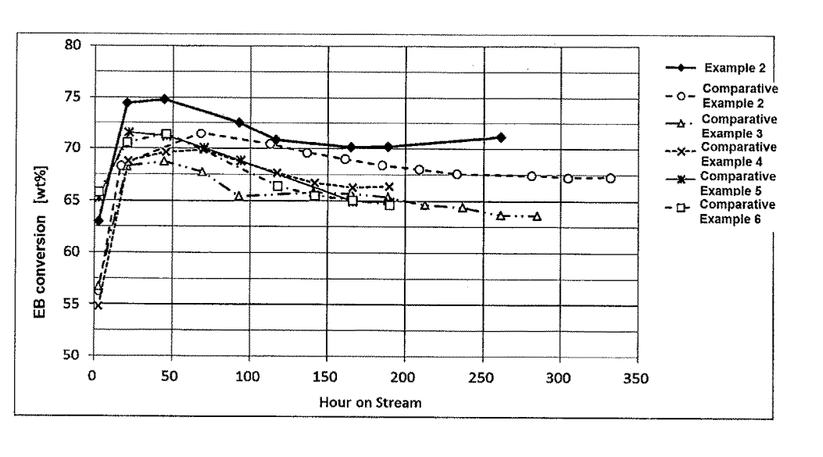
FIG. 1 shows the changes in EB conversion over reaction time for catalysts in Comparative Examples 3 to 6 and catalysts in Example 2 and Comparative Example 2.

FIG. 1 shows the EB conversion changes over reaction time for the catalysts in Comparative Examples 3 to 6 and the aforementioned catalysts in Example 2 and Comparative Example 2. For the catalysts other than the catalyst in Comparative Example 6, the reaction temperature was changed from 620° C. to 600° C., 570° C. or 540° C. after the reaction test shown in FIG. 1, and products recovered from the reactor at the respective reaction temperatures were analysed, and the conversion of ethylbenzene (EB conversion) and the selectivity to styrene (SM selectivity) were calculated. The EB conversions at different temperatures and SM selectivity at a 50% EB conversion for each catalyst are shown in Table 3.

TABLE 2

| | Yttrium compound or dysprosium compound (form in adding) | EB conversion [%] at different reaction temperatures | | | | SM SELECTIVITY [%] AT 50% EB CONVERSION |
|---|---|---|---|---|---|---|
| | | 620° C. | 600° C. | 570° C. | 540° C. | |
| Comparative Example 2 | none | 67.3 | 55.3 | 35.5 | 18.6 | 98.3 |
| Example 2 | Y(NO3)3•6H2O (aqueous solution) | 71.2 | 60.3 | 41.3 | 23.4 | 98.2 |
| Example 3 | Y2O3 (powder) | 70.4 | 60.1 | 40.7 | 23.1 | 98.3 |
| Example 4 | Dy (NO3)3•5H2O (aqueous solution) | 69.1 | 58.1 | 39.4 | 22.1 | 98.3 |

From the above Examples and Comparative Examples, catalysts containing an yttrium compound were proved to exhibit a higher conversion than conventional catalysts containing no yttrium compound. The addition of an yttrium compound to a catalyst in the present invention does not affect the styrene selectivity. In addition, catalysts containing a dysprosium compound were proved to exhibit a higher conversion than conventional catalysts containing no dysprosium compound. The addition of a dysprosium compound to a catalyst in the present invention does not affect the styrene selectivity.

TABLE 3

| | Raw material compound additionally added to Comparative Example 2 | EB conversion [%] at different reaction temperatures | | | | SM SELECTIVITY [%] AT 50% EB CONVERSION |
|---|---|---|---|---|---|---|
| | | 620° C. | 600° C. | 570° C. | 540° C. | |
| Example 2 | Y(NO3)3•6H2O (aqueous solution) | 71.2 | 60.3 | 41.3 | 23.4 | 98.2 |
| Comparative Example 2 | none | 67.3 | 55.3 | 35.5 | 18.6 | 98.3 |
| Comparative Example 3 | KVO$_3$ | 63.8 | 53.1 | 30.6 | 15.9 | 98.3 |
| Comparative Example 4 | WO$_3$ | 66.4 | 56.8 | 34.4 | 17.9 | 98.2 |
| Comparative Example 5 | Cr$_2$O$_3$ | 64.9 | 52.9 | 33.8 | 16.7 | 97.9 |

When the catalysts in Example 1 and Comparative Example 1 were taken out after the reaction test and visually observed, no noticeable damage was found for both of the pellets. From these results, the addition of yttrium was considered to cause no lowering of the mechanical strength at least in comparison with case without such an addition, and thus determined as being sufficiently preferable for practical use.

The above results are summarised as follows.

1) Fe—K—Ce—Y System

Comparing the four-component system (Example 1) with Comparative Example 1 without Y, the addition of Y improves the EB conversion at any of the temperatures. From calculation of the difference in the conversion between Example 1 and Comparative Example 1 for each of the temperatures 620° C., 600° C., 570° C. and 540° C. (Table 4), it is clear that the catalyst containing Y has high activity even in low-temperature regions.

TABLE 4

| | EB conversion [%] at different reaction temperatures | | | |
|---|---|---|---|---|
| | 620° C. | 600° C. | 570° C. | 540° C. |
| Example 1 (Fe—K—Ce—Y system) | 65.4 | 55.3 | 40.3 | 21.7 |
| Comparative Example 1 (Fe—K—Ce system) | 63.9 | 51.9 | 37.2 | 17.9 |
| Difference in EB conversion between Example 1 and Comparative Example 1 | 1.5 | 3.4 | 3.1 | 3.8 |

2) Fe—K—Ce—Na—Ca—Mo—Pd—Y System

To a system with Na, Ca, Mo and Pd as cocatalysts, elements exemplified in e.g. Patent Literature 2 were further added, and the effects were compared.

The results are as follows.

(I) As can be seen from the comparison between Comparative Example 2 and Example 3, the addition of Y greatly improved the EB conversion not only in high-temperature regions but also in low-temperature regions, even in a system with cocatalysts of Ca, Mo, etc. (Table 5).

(II) Among cocatalysts exemplified in Patent Literatures 2 and 4, V, W and Cr lowered the EB conversion (Table 5).

(III) The comparison between Comparative Example 1 and Comparative Example 2 demonstrated that Ca, Mo, etc. regarded as cocatalysts in Patent Literature 1 also improve the EB conversion in high-temperature regions (Table 6). However, the activity-improving effect was not found in low-temperature regions.

(IV) As described above, the characteristic of exhibiting high activity not only in high-temperature regions but also at low temperatures was observed only for cases with the addition of Y in the above experiment, and said characteristic was not observed in cases using a non-rare earth element.

(V) From these results, it was revealed that rare earth elements, in particular, Y improves the EB conversion in a particularly wide temperature region, as a cocatalyst for use in combination with Ce. Since a temperature distribution is present in a catalyst bed in an actual apparatus for the production of styrene monomer (for example, 600 to 650° C. at the inlet of the catalyst bed and under 600° C. at the outlet), it is obvious that the Y-containing catalyst, which exhibits high activity in a wide temperature region, has a remarkable effect on the improvement of productivity. In addition, the same is applied to Dy from the result for Example 4.

TABLE 5

| | Element | EB conversion [%] at different reaction temperatures | | | |
|---|---|---|---|---|---|
| | | 620° C. | 600° C. | 570° C. | 540° C. |
| Example 3 | Y | 70.4 | 60.1 | 40.7 | 23.1 |
| Comparative Example 2 | none | 67.3 | 55.3 | 35.5 | 18.6 |
| Comparative Example 3 | V | 63.8 | 53.1 | 30.6 | 15.9 |
| Comparative Example 4 | W | 66.4 | 56.8 | 34.4 | 17.9 |
| Comparative Example 5 | Cr | 64.9 | 52.9 | 33.8 | 16.7 |

TABLE 6

| | EB conversion [%] at different reaction temperatures | | | |
|---|---|---|---|---|
| | 620° C. | 600° C. | 570° C. | 540° C. |
| Comparative Example 2 (Fe—K—Ce—Na—Ca—Mo—Pd system) | 67.3 | 55.3 | 35.5 | 18.6 |
| Comparative Example 1 (Fe—K—Ce system) | 63.9 | 51.9 | 37.2 | 17.9 |
| Difference in EB conversion between Comparative Example 2 and Comparative Example 1 | 3.4 | 3.4 | −1.7 | 0.7 |

The invention claimed is:

1. An alkylaromatic compound dehydrogenation catalyst, comprising iron (Fe), potassium (K) and cerium (Ce), and at least one rare earth element other than cerium, wherein the rare earth element is selected from the group consisting of yttrium (Y), dysprosium (Dy) and a mixture thereof, wherein iron is in an amount of 30 to 90% by weight, calculated as $Fe_2O_3$, potassium is in an amount of 1 to 50% by weight, calculated as $K_2O$, and cerium is in an amount of 1 to 50% by weight, calculated as $CeO_2$ and the rare earth element is in an amount of 0.01 to 1% by weight, calculated as an oxide of the rare earth, relative to 100% by weight of the total amount of the catalyst.

2. The catalyst according to claim 1, wherein the rare earth element is yttrium (Y).

3. The catalyst according to claim 1, wherein the rare earth element is dysprosium (Dy).

4. The catalyst according to claim 1, further comprising a Group 2 element and/or a Group 6 element.

5. The catalyst according to claim 4, wherein the amount of the Group 2 element is 0.3 to 10% by weight calculated as an oxide of the Group 2 element relative to 100% by weight of the total amount of the catalyst, and the amount of the Group 6 element is 0.1 to 10% by weight calculated as an oxide of the Group 6 element relative to 100% by weight of the total amount of the catalyst.

6. The catalyst according to claim 4, wherein the Group 2 element is calcium (Ca) and the Group 6 element is molybdenum (Mo).

7. The catalyst according to claim 6, wherein the amount of calcium is 0.3 to 10% by weight calculated as CaO relative to 100% by weight of the total amount of the catalyst, and the amount of molybdenum is 0.1 to 10% by weight calculated as $MoO_3$ relative to 100% by weight of the total amount of the catalyst.

8. The catalyst according to claim 1, further comprising an alkali metal other than potassium.

9. The catalyst according to claim 8, wherein the alkali metal other than potassium is sodium (Na).

10. A process for producing an alkenylaromatic compound, comprising a step of contacting an alkylaromatic compound with steam in the presence of the catalyst according to claim 9.

11. The catalyst according to claim 1, further comprising a Group 2 element, a Group 6 element and an alkali metal other than potassium.

12. The catalyst according to claim 11, wherein the alkali metal is sodium (Na).

13. The catalyst according to claim 12, comprising sodium in an amount of 0.001 to 15% by weight calculated as $Na_2O$ relative to 100% by weight of the total amount of the catalyst.

14. The catalyst according to claim 11, further comprising calcium, molybdenum and sodium.

15. A process for producing an alkenylaromatic compound, comprising a step of contacting an alkylaromatic compound with steam in the presence of the catalyst according to claim 14.

16. The catalyst according to claim 1, further comprising a noble metal in an amount of 0.1 to 200 ppm by weight, wherein the noble metal is selected from the group consisting of ruthenium, osmium, iridium, rhodium, platinum, palladium, silver and gold.

17. The catalyst according to claim 16, wherein the noble metal is selected from the group consisting of platinum and palladium.

18. A process for producing an alkenylaromatic compound, comprising a step of contacting an alkylaromatic compound with steam in the presence of the catalyst according to claim 17.

19. A process for producing an alkenylaromatic compound, comprising a step of contacting an alkylaromatic compound with steam in the presence of the catalyst according to claim 1.

20. The process according to claim 19, wherein the alkylaromatic compound is contacted with steam at an $H_2O$/alkylaromatic compound ratio (weight ratio) of 0.5 to 1.5.

21. The process according to claim 19, wherein the alkylaromatic compound is contacted with steam at an inlet temperature of 600° C. to 650° C. and an outlet temperature of under 600° C.

22. The process according to claim 19, wherein the alkylaromatic compound is ethylbenzene and the alkenylaromatic compound is styrene.

23. The process according to claim 19, wherein the alkylaromatic compound is contacted with steam at a pressure of 5 hPa to ambient pressure, and at LHSV of 0.3 to 1.5.

* * * * *